(12) United States Patent
Weber et al.

(10) Patent No.: US 8,066,759 B2
(45) Date of Patent: Nov. 29, 2011

(54) RESONATOR FOR MEDICAL DEVICE

(75) Inventors: Jan Weber, Maple Grove, MN (US); Matthew J. Miller, Stillwater, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1867 days.

(21) Appl. No.: 11/207,304

(22) Filed: Aug. 19, 2005

(65) Prior Publication Data

US 2006/0178576 A1 Aug. 10, 2006

Related U.S. Application Data

(60) Provisional application No. 60/650,006, filed on Feb. 4, 2005.

(51) Int. Cl.
*A61F 2/06* (2006.01)
*A61B 5/05* (2006.01)

(52) U.S. Cl. ....................... 623/1.15; 600/422

(58) Field of Classification Search .................. 623/1.1, 623/1.22, 1.15, 1.44, 1.16; 600/410, 411; 219/635, 636, 643
See application file for complete search history.

(56) References Cited

U.S. PATENT DOCUMENTS

| | | | |
|---|---|---|---|
| 5,409,460 A | 4/1995 | Krumme | 604/107 |
| 5,824,045 A | 10/1998 | Alt | 623/1 |
| 5,843,117 A | 12/1998 | Alt et al. | 606/194 |
| 5,855,600 A | 1/1999 | Alt | 623/1 |
| 5,871,437 A | 2/1999 | Alt | 600/3 |
| 6,027,510 A | 2/2000 | Alt | 606/108 |
| 6,053,873 A | 4/2000 | Govari et al. | 600/505 |
| 6,099,561 A | 8/2000 | Alt | 623/1.44 |
| 6,106,473 A | 8/2000 | Violante et al. | 600/458 |
| 6,159,142 A | 12/2000 | Alt | 600/3 |
| 6,159,237 A | 12/2000 | Alt et al. | 623/1.11 |
| 6,231,516 B1 | 5/2001 | Keilman et al. | 600/485 |
| 6,245,104 B1 | 6/2001 | Alt | 623/1.46 |
| 6,251,134 B1 | 6/2001 | Alt et al. | 623/1.16 |
| 6,280,385 B1 * | 8/2001 | Melzer et al. | 600/423 |
| 6,304,769 B1 | 10/2001 | Arenson et al. | 600/424 |
| 6,387,121 B1 | 5/2002 | Alt | 623/1.15 |
| 6,398,805 B1 | 6/2002 | Alt | 623/1.15 |
| 6,416,540 B1 | 7/2002 | Mathur | 623/1.15 |
| 6,463,317 B1 | 10/2002 | Kucharczyk et al. | 600/411 |
| 6,478,815 B1 | 11/2002 | Alt | 623/1.15 |
| 6,511,325 B1 | 1/2003 | Lalka et al. | 434/272 |
| 6,516,213 B1 | 2/2003 | Nevo | 600/424 |
| 6,574,497 B1 | 6/2003 | Pacetti | 600/420 |

(Continued)

FOREIGN PATENT DOCUMENTS

WO WO 99/42039 8/1999

(Continued)

OTHER PUBLICATIONS

International Search Report (7 pgs.).

*Primary Examiner* — Long V. Le
*Assistant Examiner* — Lawrence Laryea
(74) *Attorney, Agent, or Firm* — Brooks, Cameron & Huebsch, PLLC

(57) ABSTRACT

A resonator device for medical device is provided. The resonator device includes a helical structure and a capacitor structure. The resonator device can be used in conjunction with a medical device, including a stent.

32 Claims, 9 Drawing Sheets

U.S. PATENT DOCUMENTS

| | | | |
|---|---|---|---|
| 6,585,660 B2 | 7/2003 | Dorando et al. | 600/486 |
| 6,585,755 B2 | 7/2003 | Jackson et al. | 623/1.15 |
| 6,585,763 B1 | 7/2003 | Keilman et al. | 623/1.42 |
| 6,628,980 B2 | 9/2003 | Atalar et al. | 600/423 |
| 6,652,540 B1 | 11/2003 | Cole et al. | 606/153 |
| 6,663,570 B2 | 12/2003 | Mott et al. | 600/486 |
| 6,668,197 B1 | 12/2003 | Habib et al. | 607/101 |
| 6,673,104 B2 | 1/2004 | Barry | 623/1.15 |
| 6,676,694 B1 | 1/2004 | Weiss | 623/1.11 |
| 6,702,847 B2 | 3/2004 | DiCarlo | 623/1.34 |
| 6,711,429 B1 | 3/2004 | Gilboa et al. | 600/407 |
| 6,711,440 B2 | 3/2004 | Deal et al. | 607/9 |
| 6,712,844 B2 | 3/2004 | Pacetti | 623/1.15 |
| 6,716,237 B1 | 4/2004 | Alt | 623/1.11 |
| 6,718,203 B2 | 4/2004 | Weiner et al. | 607/2 |
| 6,718,207 B2 | 4/2004 | Connelly | 607/9 |
| 6,725,092 B2 | 4/2004 | MacDonald et al. | 607/2 |
| 6,731,979 B2 | 5/2004 | MacDonald | 607/9 |
| 6,757,566 B2 | 6/2004 | Weiner et al. | 607/116 |
| 6,760,628 B2 | 7/2004 | Weiner et al. | 607/122 |
| 6,763,268 B2 | 7/2004 | MacDonald et al. | 607/9 |
| 6,765,144 B1 | 7/2004 | Wang et al. | 174/36 |
| 6,767,360 B1 | 7/2004 | Alt et al. | 623/1.15 |
| 6,778,856 B2 | 8/2004 | Connelly et al. | 607/32 |
| 6,782,284 B1 | 8/2004 | Subramanyan et al. | 600/407 |
| 6,786,904 B2 | 9/2004 | Döscher et al. | 606/28 |
| 6,795,730 B2 | 9/2004 | Connelly et al. | 607/9 |
| 6,795,736 B2 | 9/2004 | Connelly et al. | 607/36 |
| 6,799,069 B2 | 9/2004 | Weiner et al. | 607/3 |
| 6,802,811 B1 | 10/2004 | Slepian | 600/309 |
| 6,802,857 B1* | 10/2004 | Walsh et al. | 623/1.15 |
| 6,808,535 B1 | 10/2004 | Jordan | 623/1.34 |
| 6,819,954 B2 | 11/2004 | Connelly | 607/27 |
| 6,819,958 B2 | 11/2004 | Weiner et al. | 607/116 |
| 6,829,509 B1 | 12/2004 | MacDonald et al. | 607/119 |
| 6,844,492 B1 | 1/2005 | Wang et al. | 174/36 |
| 6,845,266 B2 | 1/2005 | Weiner et al. | 607/2 |
| 6,847,837 B1 | 1/2005 | Melzer et al. | 600/421 |
| 6,850,804 B2 | 2/2005 | Eggers et al. | 607/103 |
| 6,850,805 B2 | 2/2005 | Connelly et al. | 607/122 |
| 6,875,180 B2 | 4/2005 | Weiner et al. | 600/508 |
| 6,884,234 B2 | 4/2005 | Aita et al. | 604/103.01 |
| 6,892,090 B2 | 5/2005 | Verard et al. | 600/424 |
| 6,898,454 B2* | 5/2005 | Atalar et al. | 600/410 |
| 6,901,290 B2 | 5/2005 | Foster et al. | 607/9 |
| 6,908,468 B2 | 6/2005 | Daum | 606/76 |
| 6,925,322 B2 | 8/2005 | Helfer et al. | 600/423 |
| 6,925,328 B2 | 8/2005 | Foster et al. | 607/9 |
| 6,954,674 B2 | 10/2005 | Connelly | 607/63 |
| 6,957,098 B1 | 10/2005 | Hyde et al. | 600/424 |
| 7,279,664 B2* | 10/2007 | Weber | 219/635 |
| 7,725,160 B2* | 5/2010 | Weber | 600/423 |
| 2001/0031919 A1 | 10/2001 | Strommer et al. | 600/424 |
| 2001/0031920 A1 | 10/2001 | Kaufman et al. | 600/410 |
| 2002/0019660 A1 | 2/2002 | Gianotti et al. | 623/1.15 |
| 2002/0026230 A1 | 2/2002 | Moll et al. | 623/1.13 |
| 2002/0045815 A1 | 4/2002 | Van Vaals | 600/411 |
| 2002/0045816 A1 | 4/2002 | Atalar et al. | 600/423 |
| 2002/0049375 A1 | 4/2002 | Strommer et al. | 600/407 |
| 2002/0082679 A1 | 6/2002 | Sirhan et al. | 623/1.15 |
| 2002/0082685 A1 | 6/2002 | Sirhan et al. | 623/1.42 |
| 2002/0137014 A1 | 9/2002 | Anderson et al. | 434/262 |
| 2002/0173724 A1 | 11/2002 | Dorando et al. | 600/486 |
| 2002/0188345 A1 | 12/2002 | Pacetti | 623/1.15 |
| 2003/0004562 A1 | 1/2003 | DiCarlo | 623/1.13 |
| 2003/0004563 A1 | 1/2003 | Jackson et al. | 623/1.15 |
| 2003/0074049 A1 | 4/2003 | Hoganson et al. | 623/1.13 |
| 2003/0083579 A1 | 5/2003 | Aita et al. | 600/470 |
| 2003/0087244 A1 | 5/2003 | McCarthy | 435/6 |
| 2003/0088178 A1 | 5/2003 | Owens et al. | 600/420 |
| 2003/0088308 A1 | 5/2003 | Scheuermann et al. | 623/1.15 |
| 2003/0092013 A1 | 5/2003 | McCarthy | 435/6 |
| 2003/0096248 A1 | 5/2003 | McCarthy et al. | 435/6 |
| 2003/0099957 A1 | 5/2003 | McCarthy | 435/6 |
| 2003/0100830 A1 | 5/2003 | Zhong et al. | 600/431 |
| 2003/0105069 A1 | 6/2003 | Robinson et al. | 514/185 |
| 2003/0139739 A1 | 7/2003 | Doscher et al. | 606/28 |
| 2003/0143544 A1 | 7/2003 | McCarthy | 435/6 |
| 2003/0144728 A1 | 7/2003 | Scheuermann et al. | 623/1.15 |
| 2003/0149475 A1* | 8/2003 | Hyodoh et al. | 623/1.19 |
| 2003/0163052 A1 | 8/2003 | Mott et al. | 600/486 |
| 2003/0187335 A1 | 10/2003 | McCarthy | 600/300 |
| 2003/0199747 A1 | 10/2003 | Michlitsch et al. | 600/407 |
| 2003/0212448 A1 | 11/2003 | Smith | 623/1.13 |
| 2004/0010304 A1 | 1/2004 | Weber et al. | 623/1.11 |
| 2004/0019376 A1 | 1/2004 | Alt | 623/1.42 |
| 2004/0030379 A1 | 2/2004 | Hamm et al. | 623/1.15 |
| 2004/0034300 A1 | 2/2004 | Verard et al. | 600/424 |
| 2004/0038406 A1 | 2/2004 | Unger et al. | 435/459 |
| 2004/0039438 A1 | 2/2004 | Alt | 623/1.15 |
| 2004/0044397 A1 | 3/2004 | Stinson | 623/1.15 |
| 2004/0059280 A1 | 3/2004 | Makower et al. | 604/8 |
| 2004/0082866 A1 | 4/2004 | Mott et al. | 600/486 |
| 2004/0091603 A1 | 5/2004 | Priewe | 427/2.24 |
| 2004/0093075 A1 | 5/2004 | Kuehne | 623/1.15 |
| 2004/0097804 A1 | 5/2004 | Sobe | 600/424 |
| 2004/0097805 A1 | 5/2004 | Verard et al. | 600/428 |
| 2004/0098093 A1 | 5/2004 | DiCarlo | 623/1.13 |
| 2004/0111016 A1 | 6/2004 | Casscells, III et al. | 600/310 |
| 2004/0116997 A1 | 6/2004 | Taylor et al. | 623/1.11 |
| 2004/0117007 A1 | 6/2004 | Whitbourne et al. | 623/1.42 |
| 2004/0122494 A1 | 6/2004 | Eggers et al. | 607/103 |
| 2004/0143180 A1 | 7/2004 | Zhong et al. | 600/410 |
| 2004/0158310 A1 | 8/2004 | Weber et al. | 623/1.15 |
| 2004/0186377 A1 | 9/2004 | Zhong et al. | 600/431 |
| 2004/0210289 A1 | 10/2004 | Wang et al. | 607/116 |
| 2004/0230271 A1 | 11/2004 | Wang et al. | 607/116 |
| 2004/0243220 A1 | 12/2004 | Gianotti et al. | 623/1.15 |
| 2004/0249428 A1 | 12/2004 | Wang et al. | 607/116 |
| 2004/0254419 A1 | 12/2004 | Wang et al. | 600/8 |
| 2004/0254632 A1 | 12/2004 | Alt et al. | 623/1.15 |
| 2005/0004653 A1 | 1/2005 | Gerberding et al. | 623/1.13 |
| 2005/0025797 A1 | 2/2005 | Wang et al. | 424/422 |
| 2005/0033407 A1 | 2/2005 | Weber et al. | 623/1.15 |
| 2005/0049480 A1 | 3/2005 | Gray | 600/407 |
| 2005/0049481 A1 | 3/2005 | Gray et al. | 600/407 |
| 2005/0049482 A1 | 3/2005 | Gray et al. | 600/407 |
| 2005/0049683 A1 | 3/2005 | Gray et al. | 623/1.15 |
| 2005/0049684 A1 | 3/2005 | Gray et al. | 623/1.15 |
| 2005/0049685 A1 | 3/2005 | Gray et al. | 623/1.15 |
| 2005/0049686 A1 | 3/2005 | Gray et al. | 623/1.15 |
| 2005/0049688 A1 | 3/2005 | Gray et al. | 623/1.16 |
| 2005/0049689 A1 | 3/2005 | Gray et al. | 623/1.16 |
| 2005/0065430 A1 | 3/2005 | Wiethoff et al. | 600/413 |
| 2005/0065437 A1 | 3/2005 | Weber et al. | 600/431 |
| 2005/0079132 A1 | 4/2005 | Wang et al. | 424/1.11 |
| 2005/0080459 A1* | 4/2005 | Jacobson et al. | 607/9 |
| 2005/0085895 A1 | 4/2005 | Brown et al. | 623/1.15 |
| 2005/0090886 A1 | 4/2005 | MacDonald et al. | 607/122 |
| 2005/0107870 A1 | 5/2005 | Wang et al. | 623/1.44 |
| 2005/0113669 A1 | 5/2005 | Helfer et al. | |
| 2005/0113676 A1 | 5/2005 | Weiner et al. | 600/421 |
| 2005/0113873 A1 | 5/2005 | Weiner et al. | 607/2 |
| 2005/0113874 A1 | 5/2005 | Connelly et al. | 607/2 |
| 2005/0113876 A1 | 5/2005 | Weiner et al. | 607/36 |
| 2005/0131522 A1 | 6/2005 | Stinson et al. | 623/1.15 |
| 2005/0143651 A1 | 6/2005 | Verard et al. | 600/424 |
| 2005/0149002 A1 | 7/2005 | Wang et al. | 606/1 |
| 2005/0149157 A1 | 7/2005 | Hunter et al. | 607/119 |
| 2005/0149169 A1 | 7/2005 | Wang et al. | 623/1.15 |
| 2005/0152946 A1 | 7/2005 | Hunter et al. | 424/423 |
| 2005/0154374 A1 | 7/2005 | Hunter et al. | 604/890.1 |
| 2005/0155779 A1 | 7/2005 | Wang et al. | 174/35 |
| 2005/0158356 A1 | 7/2005 | Hunter et al. | 424/423 |
| 2005/0159661 A1 | 7/2005 | Connelly et al. | 600/410 |
| 2005/0165470 A1 | 7/2005 | Weber | 623/1.15 |
| 2005/0165471 A1 | 7/2005 | Wang et al. | 623/1.15 |
| 2005/0169960 A1 | 8/2005 | Hunter et al. | 424/423 |
| 2005/0169961 A1 | 8/2005 | Hunter et al. | 424/423 |
| 2005/0175664 A1 | 8/2005 | Hunter et al. | 424/423 |
| 2005/0175665 A1 | 8/2005 | Hunter et al. | 424/423 |
| 2005/0175703 A1 | 8/2005 | Hunter et al. | 424/486 |
| 2005/0178395 A1 | 8/2005 | Hunter et al. | 128/898 |
| 2005/0178396 A1 | 8/2005 | Hunter et al. | 128/898 |
| 2005/0178584 A1 | 8/2005 | Wang et al. | 174/256 |
| 2005/0181005 A1 | 8/2005 | Hunter et al. | 424/422 |
| 2005/0181009 A1 | 8/2005 | Hunter et al. | 424/423 |

| | | | | | | |
|---|---|---|---|---|---|---|
| 2005/0181010 A1 | 8/2005 | Hunter et al. ............... 424/423 | 2005/0209664 A1 | 9/2005 | Hunter et al. ............... 607/115 |
| 2005/0182450 A1 | 8/2005 | Hunter et al. ............... 607/36 | 2005/0209665 A1 | 9/2005 | Hunter et al. ............... 607/115 |
| 2005/0182463 A1 | 8/2005 | Hunter et al. ............... 607/115 | 2005/0209666 A1 | 9/2005 | Hunter et al. ............... 607/115 |
| 2005/0182467 A1 | 8/2005 | Hunter et al. ............... 607/116 | 2005/0215764 A1 | 9/2005 | Tuszynski et al. ........... 530/358 |
| 2005/0182468 A1 | 8/2005 | Hunter et al. ............... 607/116 | 2005/0216075 A1 | 9/2005 | Wang et al. ............... 623/1.15 |
| 2005/0182469 A1 | 8/2005 | Hunter et al. ............... 607/116 | 2006/0105016 A1* | 5/2006 | Gray et al. .................. 424/423 |
| 2005/0183731 A1 | 8/2005 | Hunter et al. ............... 128/898 | 2006/0106454 A1* | 5/2006 | Osborne et al. ............ 623/1.24 |
| 2005/0186239 A1 | 8/2005 | Hunter et al. ............... 424/422 | 2006/0136039 A1* | 6/2006 | Martin ....................... 623/1.16 |
| 2005/0186244 A1 | 8/2005 | Hunter et al. ............... 424/423 | | | |
| 2005/0186245 A1 | 8/2005 | Hunter et al. ............... 424/423 | | | |
| 2005/0187140 A1 | 8/2005 | Hunter et al. ............... 514/2 | | | |
| 2005/0187582 A1 | 8/2005 | Weiner ......................... 607/4 | | | |
| 2005/0187600 A1 | 8/2005 | Hunter et al. ............... 607/115 | | | |
| 2005/0192647 A1 | 9/2005 | Hunter et al. ............... 607/57 | | | |
| 2005/0196421 A1 | 9/2005 | Hunter et al. ............... 424/423 | | | |
| 2005/0208095 A1 | 9/2005 | Hunter et al. ............... 424/423 | | | |

FOREIGN PATENT DOCUMENTS

| | | |
|---|---|---|
| WO | WO 99/42176 | 8/1999 |
| WO | WO 01/74241 | 10/2001 |
| WO | WO 02/094339 | 11/2002 |
| WO | WO 97/21401 A1 | 6/2007 |

* cited by examiner

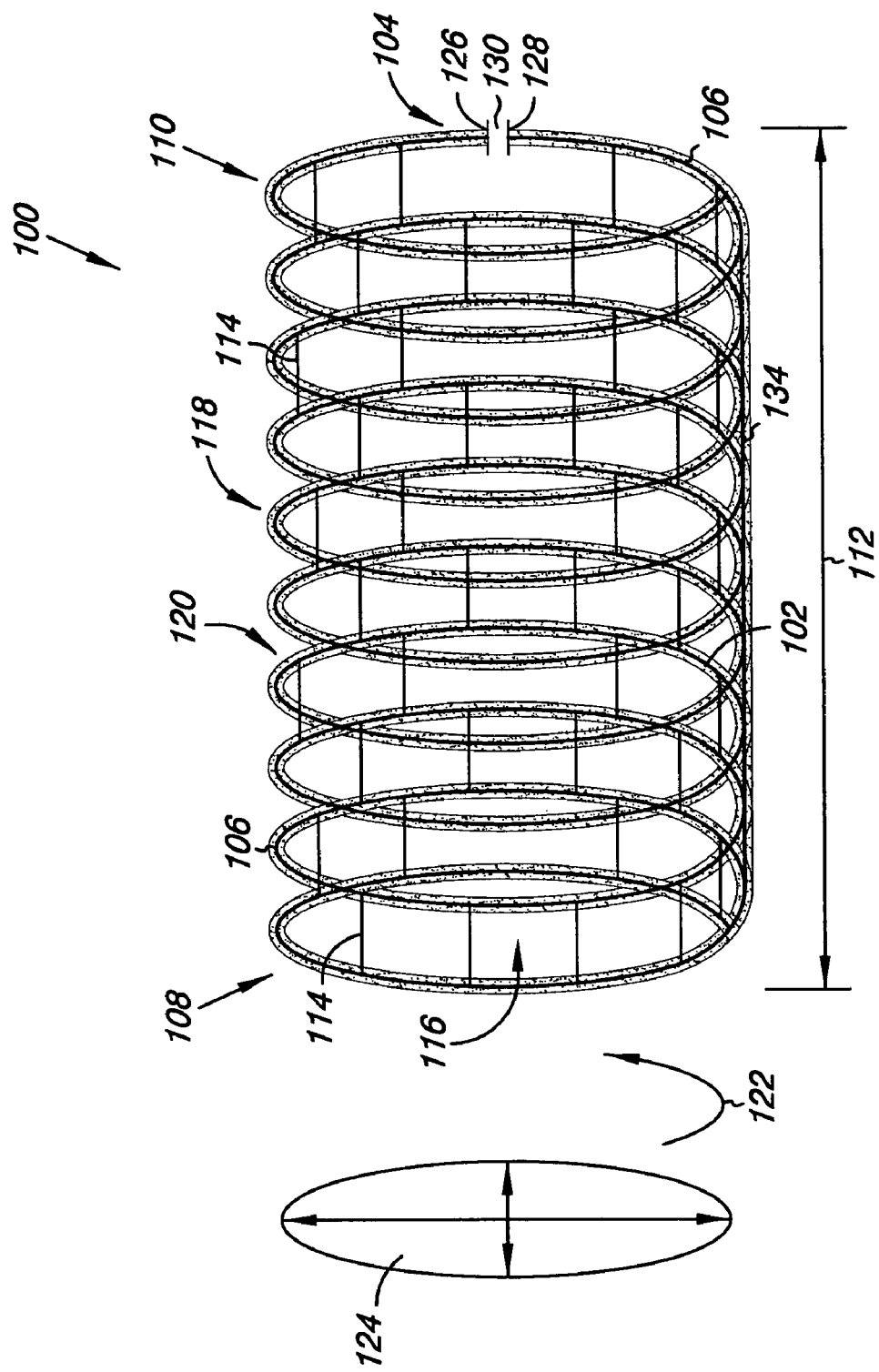

RESONATOR FOR MEDICAL DEVICE

This application claims priority from U.S. Provisional Application Ser. No. 60/650,006, filed Feb. 4, 2005, the entire content of which is incorporated herein by reference.

FIELD OF THE INVENTION

The present invention relates generally to medical device apparatus, systems, and methods; and more particularly to medical device apparatus; systems, and methods for use during magnetic resonance imaging.

BACKGROUND

Stents and other metallic implants can cause a partial shielding of a radio frequency (RF) field by the Faraday Effect. In essences, the stent acts like a "Faraday Cage" that prevents the RF field from penetrating to the interior of the stent. Because stents are not ideal but only partial Faraday cages, a small percentage of the RF field still is able to penetrate to the interior, however not enough to cause enough spins to flip over and give a reasonable visibility.

One approach to achieving the reasonable visibility would be to raise the energy of the RF field (the flip-angle that stands for the duration of the RF-pulse) to such high levels that enough energy remains after passing through the partial stent shield for visualization. Unfortunately, taking this approach will cause the tissue of the body to be heated to unacceptable levels.

BRIEF DESCRIPTION OF THE DRAWINGS

The illustrations provided in the Figures are not to scale.

FIG. 1 illustrates an embodiment of a resonator device according to the present invention.

DETAILED DESCRIPTION

Figure 2A:
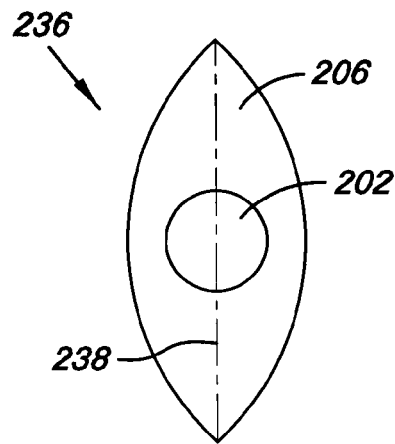
FIGS. 2A-2C illustrate embodiments of portions of a resonator device according to the present invention.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide a number of additional embodiments of valve. In addition, discussion of features and/or attributes for an element with respect to one Fig. can also apply to the element shown in one or more additional Figs.

Embodiments of the present invention are directed to medical device apparatus, systems, and methods of using the medical device. Generally, the medical device includes a resonator to be used in conjunction with an additional medical device, referred to herein as a second medical device. These second medical devices include devices that traditionally have produced artifacts (signal loss) in images obtained by magnetic resonance imaging (MRI) systems. Embodiments of the present invention address the problem of artifacts (signal loss) produced in magnetic resonance (MR) images in addition to allowing for more complete MR images to be obtained from the second medical device.

Examples of the second medical device include, but are not limited to, stents and/or shunts as are used in dialysis, artificial veins, arteries and grafts, esophageal stenosis, esophageal cancer, esophageal varacies, lung bronchi for cancer treatment, urethra, hydrocephalus shunt tubes, trachea, middle ear tubes, lymphatic ducts and grafts, gastrointestinal stenosis and inflammatory diseases (e.g. Crohn's disease), pyloric stenosis, implantable sensing devices, intravascular blood pressure devices, and biliary atresia. Examples of other types of second medical devices are also possible.

Typically, artifacts in MR images are due in large part to distortions in the magnetic field caused by an implanted medical device, such as the second medical devices discussed herein. For example, metallic stents can cause susceptibility and radiofrequency artifacts in MR images that do not allow for complete visualization of the stent lumen by magnetic resonance angiography (MRA). This is due to susceptibility artifacts and radiofrequency shielding of the metallic stents. Embodiments of the present invention can provide the potential for reduced artifacts during MR imaging with different MRA techniques through the use of a resonator device in conjunction with the second medical device (e.g., metallic vascular stent).

FIG. 1 illustrates one embodiment of a resonator device 100 of the present invention. The resonator device 100 includes an induction coil 102 that is electrically conductive and a capacitor 104 coupled in series to the induction coil 102. The resonator device 100 further includes an electrically non-conductive structural support 106 positioned over at least a portion of the induction coil and/or the capacitor 104.

As discussed herein, the induction coil 102 and the capacitor 104 of the resonator device 100 can interact with a radio frequency field of a magnetic resonance imaging (MRI) system to reduce signal loss in MR images. So, for example, the resonator device 100 could be used in combination with the second medical device (e.g., a metallic vascular stent) that if used alone would produce an artifact (signal loss) in MR images obtained by the MRI system.

As illustrated, the induction coil 102 includes an elongate configuration that extends circumferentially from a first end 108 to a second end 110 of the resonator device 100. For example, the induction coil 102 can have a helical structure as illustrated in FIG. 1 that extends from the first end 108 to the second end 110 of the device 100. In one embodiment, coils of the helical structure can be equally spaced from each other.

In an alternative embodiment, coils of the helical structure can have a predetermined non-consistent spacing relative to each other along the helical structure.

In one embodiment, the induction coil 102 can extend continuously down the length 112 of the resonator device 100 (i.e., the induction coil 102 does not deviate along the length 112 of the resonator device 100). Alternatively, the induction coil 102 can include a "zig-zag" configuration as the induction coil 102 extends down the length 112 of resonator device 100. As will be appreciated, other shapes and configurations that can act as an induction coil, besides helical coils, are also possible.

The induction coil 102 can be formed of one or more conductive members (e.g., two or more members in parallel). In addition, different cross-sectional geometries can be used for the induction coil 102. For example, the cross-sectional geometries can include circular rectangular, oval and/or polygonal, among others. Other shapes are also possible.

The conductive members of the induction coil 102 can also have a number of different sizes and structural configurations. For example, the conductive members can have a size and a shape sufficient to maintain a predetermined shape of the induction coil 102 in its deployed state. Alternatively, the size and the shape of each of the induction coil 102 and the structural support 106, as will be discussed herein, are configured to maintain the predetermined shape of the induction coil 102 in its deployed state. For example, the induction coil 102 can be configured as a thin film that resides on, or just below, a surface of the structural support 106.

In one embodiment, the conductive members of the induction coil 102 can be a metal or metal alloy. Examples of such metals and metal alloys include, but are not limited to, platinum, titanium, stainless steel (e.g., 316L stainless steel), and memory metals alloys such as Nitinol, titanium-palladuim-nickel, nickel-titanium-copper, gold-cadmium, iron-zinc-copper-aluminum, titanium-niobium-aluminum, hafnium-titanium-nickel, iron-maganese-silicon, nickel-titanium, nickel-iron-zinc-aluminum, copper-aluminum-iron, titanium-niobium, zirconium-copper-zinc, and nickel-zirconium-titanium. Other metal and metal alloys are also possible.

In addition, one or more of the components of the resonator device 100 can be made radioopaque. For example, one or more portions of the induction coil 102 could be clad with a radioopaque material to make the resonator device 100 radioopaque. Alternatively, one or more discrete radioopaque markers having a predetermined shape can be added to predetermined portions of the resonator device 100. Example of suitable materials for the radioopaque markers include, but are not limited to, copper, tungsten, gold, silver, platinum and alloys thereof.

The induction coil 102 can further include spacers 114 positioned between the turns of the induction coils 102. In one embodiment, the spacers 114 provide for electrical insulation, structural support, and structural spacing for adjacent turns of the coil 102. Spacers 114 can be coupled to the induction coil 102 in a number of ways. For example, a pair of spacers 114 could be sandwiched around the induction coil 102 and bonded with heat and/or chemical adhesive. Spacers 114 could be wound, twisted and/or braided around each other and the induction coil 102. The spacers 114 could then be bonded with heat and/or chemical adhesive.

Examples of suitable materials for the spacers 114 include, but are not limited to non-biodegradable and/or biodegradable materials. Examples of non-biodegradable materials include, but are not limited to, ceramic, polystrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersons (BAYHDROL); squalene emulsions; and mixtures and copolymers of any of the foregoing.

Examples of biodegradable materials include, but are not limited to, polycarboxylic acid, polyanhydrides including maleic anhydride polymers; polyorthoesters; poly-amino acids; polyethylene oxide; polyphosphazenes; polyactic acid, polyglycolic acid and copolymers and copolymers and mixtures thereof such as poly(L-lactic acid) (PLLA), poly (D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocaronates, and polydimethyltrimethylcarbonates; cyanoacrylate; calcium phosphates; polyglycosaminoglycans; macromolecules such as polysaccharides (including hyaluronic acid, cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

The spacers 114 and/or the structural support 106 can further include one or more therapeutic agents. In one embodiment, the one or more therapeutic agents can be integrated into the material matrix of and/or coated on the surface of the spacers 114 and/or the structural support 106. The one or more therapeutic agents can then leach and/or be released from the spacers 114 and/or the structural support 106 once implanted.

Examples of therapeutic agents include, but are not limited to, pharmaceutically acceptable agents such as non-genetic therapeutic agents, a biomolecule, a small molecule, or cells. Exemplary non-genetic therapeutic agents include anti-thrombogenic agents such as heparin, heparin derivatives, prostaglandin (including micellar prostaglandin E1), urokinase, and PPack (dextrophyenylalanine proline arginine chloromethylketone); anti-proliferative agents such as enoxaprin, angiopenptin, sirolimus (rapamycin), tacrolimus, everolimus monoclonal antibodies capable of blocking smooth muscle cell proliferation, hirudin, and acetylsalicylic acid; anti-inflammatory agents such as dexamethasone, rosiglitazone, prenisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis(2-aminoethyl)ethyleneglycol-N,N,N',N'-tetraacetic acid and mixtures thereof; antibiotics such as gentamycin rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above.

Exemplary biomolecules includes peptides, polypeptides and proteins; oligonucleotides; nucleic acids such as double or single stranded DNA (including naked and cDNA), RNA, antisense nucleic acids such as antisense DNA and RNA, small interfering RNA (siRNA), and riobozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1") and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-linear example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative (Lin-) cells including Lin-CD34-, Lin-CD34+, Lin-cKit+, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts+5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

The therapeutic agents may be combined to the extent such combination is biologically compatible.

The elongate configuration of the induction coil 102 also defines a coil lumen 116 and a peripheral surface 118 opposite the lumen 116. The induction coil 102, the capacitor 104 and the structural support 106 are configured to allow the lumen 116 to expand from a first cross-sectional size in an un-deployed state to a second cross-sectional size in a deployed state. This allows the resonator device 100 to be introduced into a body with the first cross-sectional size and then be expanded to the second cross-sectional size at the predetermined location within the body. For example, the resonator device 100 can be positioned over a balloon of a balloon catheter in its first cross-sectional size (e.g., its un-deployed configuration). The balloon can then be inflated to expand the resonator device 100 to its second cross-sectional size (e.g., its deployed configuration). Alternatively, when the induction coil 102 is formed of a memory metal alloy (such as Nitinol), the resonator device 100 can be introduced into the body in its first cross-sectional size (e.g., its un-deployed configuration) and then released to expand the resonator device 100 to its second cross-sectional size (e.g., its deployed configuration).

In one embodiment, the diameter of coil lumen 116 can be essentially equal along the length 112 of the resonator device 100. In an alternative embodiment, the expandable diameter of the coil lumen 116 changes from the first end 108 to the second end 110 of the induction coil 102. For example, the diameter of the coil lumen 116 can increase or decrease from the first end 108 to the second end 110 of the induction coil 102. Alternatively, the diameter of the coil lumen 116 can increase from the first end 108 to a predetermined point between the first and second ends 108, 110 then decrease again as the coil 102 extends to the second end 110. Other configurations are also possible.

As will be appreciated, the present embodiment allows the resonator device 100 to be used in conjunction with a second medical device that may or may not already be implanted into the body. For example, the resonator device 100 could be implanted at least partially within the lumen of a vascular stent that is already in position within a patient. Alternatively, the resonator device 100 could be positioned relative the second medical device prior to their implantation. The two devices could then be implanted together, although not necessarily at the exact same time. Examples of such configurations are discussed herein.

As will be appreciated, the induction coil 102 includes loops 120 of electrically conductive material that in conjunction with the capacitor 104 can be used to tune the resonator device 100 to a predetermined radio frequency (RF). Examples of parameters used in tuning the resonator device 100 include, but are not limited to, the number of turns 122, and the cross sectional area 124 of the induction coil 102 of the resonator device 100, as will be appreciated. In one embodiment, the number of turns 122 of the induction coil 102 can be modified based on a configuration of induction coil 102.

The configuration of the capacitor 104 of the resonator device 100 can also be modified in tuning the resonator device 100. For example, the capacitor 104 includes at least a first capacitor plate 126, a second capacitor plate 128 and a dielectric material 130 disposed between the first and second capacitor plates 126 and 128.

Predetermined modifications to the size, shape, distance between the capacitor plates and dielectric material configuration, for example, can allow for adjustments to be made in the tuning of the resonator device 100.

As will be appreciated, a plate structure need not be used for the first and second capacitor plate 126 and 128, as other shapes for the capacitor plates are possible. For example, helical coils of conductive material separated by the dielectric can be used in forming the capacitor plates. Alternatively, fractal capacitor structures could be used in providing the capacitor 104. In addition, the resonator device 100 can further include an auto-tuning circuit so as to provide additional tuning of the capacitor and/or the resonator device 100 due to, for example, changes in the diameter of the induction coil 102.

As illustrated, the resonator device 100 also includes a return conductor 134 that helps to couple the capacitor 104 positioned near the second end 110 in series to the induction coil 102 that extends between the first and second ends 108 and 110. In one embodiment, the return conductor 134 can be positioned adjacent the peripheral surface 118 of the induction coil 102. In an alternative embodiment, the return conductor 134 can be positioned within the lumen 116 of the induction coil 102.

As illustrated, the structural support 106 is positioned over at least a portion of the induction coil and/or the capacitor 104. As used herein, the structural support 106 includes both the material and the configuration (e.g., the shape) sufficient to help hold and/or maintain a shape imparted to the induction coil 102 and capacitor 104. The structural support 106 can also provide electrical insulation and heat transfer characteristics to the induction coil 102 and capacitor 104. In one embodiment, as an electrical insulator the structural support 106 can confine the induced electric current path to the induction coil 102 and the capacitor 104. With respect to heat transfer, the structural support 106 has a thermal conductivity of sufficiently high value to transfer heat generated in the induction coil 102 to the surrounding environment.

In one embodiment, the material(s) chosen for use as the structural support 106 can include mechanical properties, such as flexibility, modulus, ductile and yield properties, that can help hold and/or maintain a shape imparted to the induction coil 102 and capacitor 104. In addition, the shape and position of the structural support 106 relative the induction coil 102 and capacitor 104 can also be used to impart structural support to the resonator device 100. For example, the cross-section shape of the structural support 106 can be selected so as to help improve the flexural strength of the resonator device 100.

In one embodiment, the structural support 106 is provided as a continuous sheath that extends longitudinally with and encases the induction coil 102. As used herein, encase means to completely enclose all the exterior surfaces of the induction coil 102 so that no surfaces of the induction coil 102 are peripheral to those of the structural support 106. For example, the structural support 106 in its continuous sheath form can have a uniform wall thickness over the induction coil 102. Alternatively, the walls of the structural support 106 can have a non-uniform thickness in a predetermined shape configured to resist either bending and/or collapsing from predictable forces applied to the induction coil 102. Alternatively, the structural support 106 can have a cross-sectional profile that works in conjunction with the shape of the induction coil 102 to provide support to the coil 102. For example, the structural support 106 can include walls that are configured to resist non-uniform deformation of the induction coil 102.

Examples of suitable materials for the structural support 106 include thermoplastics selected from the group consisting of a polyamide, a polymethyl methacylate (PMMA), a polyethylene (e.g., high density polyethylene), a polyethylene terephthalate, a polyfluoroethylene, a polytetrafluoroethylene (e.g., e-PTFE), a polyetheretherketone, a polypropylene, or a polyester.

In addition, oriented support fibers can also be embedded in the structural support 106. Examples of such oriented support fibers can be included in a laminated composite, in which the structural support 106 is reinforced with fiber-reinforcing materials oriented along lines of stress in the material. In addition, the fiber-reinforcing materials can also help hold and/or maintain a shape imparted to the induction coil 102 and capacitor 104. In one embodiment, oriented fiber components of various geometries are provided by laying fibers in specific orientation over a curved mold to which a polymer material, as discussed herein, is applied. Examples of suitable support fibers can include, but are not limited to, carbon fibers, polyester fibers, aramid fibers, and also polyethylene fibers.

Figure 2B:
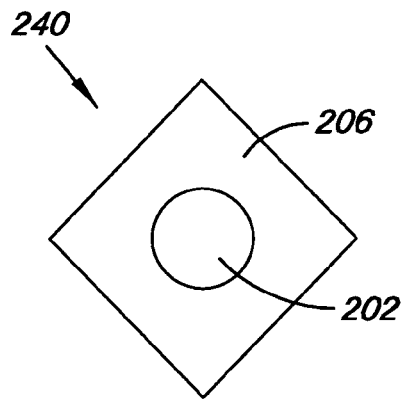
Figure 2C:
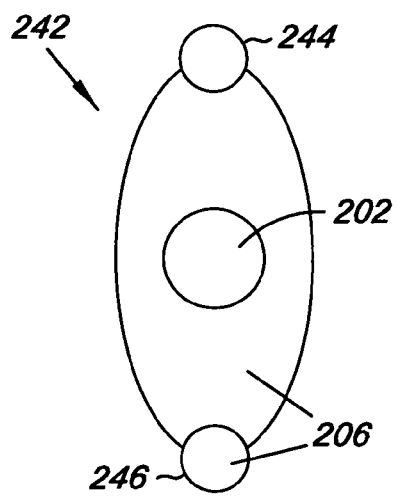

FIG. 2A-2C provide illustrations of the structural support 206 according to different embodiment so the present invention. As illustrated, the structural support 206 can have walls with non-uniform thickness in a predetermined shape configured to resist either bending and/or collapsing from predictable forces applied to the induction coil 202.

For example, FIG. 2A provides an embodiment in which the cross-sectional configuration of the structural support 206 has an elliptical shape 236. In one embodiment, the material of the structural support 206 along a major axis 238 of the elliptical shape 236 can be configured to bear compressive forces that would otherwise collapse the induction coil structure 202.

FIG. 2B provides an additional embodiment in which the cross-sectional configuration of the structural support 206 has a rhombus shape 240 that can be configured to bear compressive forces that would otherwise collapse the induction coil structure 202. FIG. 2C provides an additional embodiment in which the cross-sectional configuration of the structural support 206 has a multi-component construction 242. As illustrated, the multi-component construction 242 can include two or more parts whose cross-sectional shape can synergistically interact to bear the compressive forces that would otherwise collapse the induction coil structure 202. In one embodiment, the multi-component construction 238 can include a first member 244 coupled to a second member 246, where each member can be formed of the same material or different material.

Figure 3:
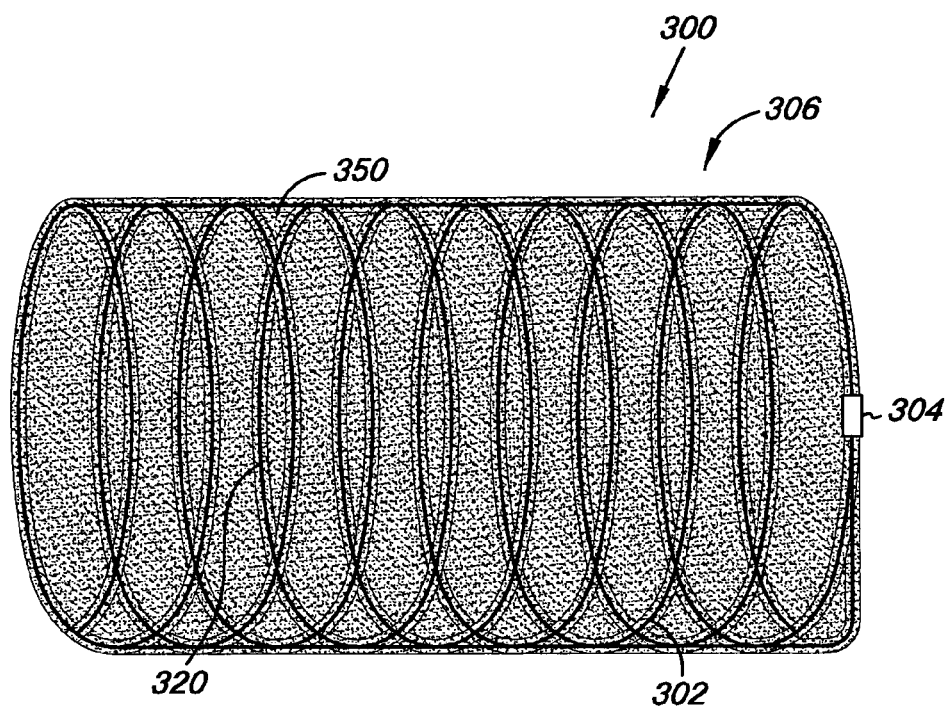
FIG. 3 illustrates an embodiment of a resonator device according to the present invention.

FIG. 3 provides an additional embodiment of the structural support 306 in relation to the induction coil 302 and capacitor 304. As illustrated, the structural support 306 is in the form of a tube 350 that supports the induction coil 302 and the capacitor 304. In one embodiment, the induction coil 302 and capacitor 304 are encased between opposite layers of the cover 306. In one embodiment, this can be accomplished by a bonding process through the application of heat and/or chemical adhesives.

In an alternative embodiment, the structural support 306 could be formed around the induction coil 302 and capacitor 304. In other words, the induction coil 302 and capacitor 304 could be embedded in the cover 306. In one embodiment, this type of configuration helps to maintain the relative position of the loops 320 of the induction coil 302 and capacitor 304. In one embodiment, the structural support 306 can be in the form of strips of material that are wrapped around both the exterior and interior sides of the induction coil 302 and capacitor 304. Alternatively, the induction coil 302 and capacitor 304 can be dip-coated (e.g., in a solution of the structural support material) so as to create the structural support 306.

In one embodiment, the structural support 306 can be in the form of an extruded tube. Alternatively, the tubular structure of the structural support 306 can be formed by a weaving or knitting process using one or more filaments, or multi-filament yarn, of the cover material as described herein. In addition, the structural support 306 can have a wall thickness of 100 micrometers or less. As will be appreciated, the structural support 306 may also be coated with one or more therapeutic compounds such as anticoagulant, anti-inflammatory, pro-endothelization compounds, among others.

In an additional embodiment, the induction coil 302 and capacitor 304 can reside on a surface of the structural support 306. For example, the induction coil 302 and/or the capacitor 304 can be positioned on a peripheral surface of the structural support 306. Alternatively, the induction coil 302 and/or the capacitor 304 can be positioned on an interior surface (defining the lumen) of the structural support 306. As discussed herein, the induction coil 302 can be in the form of a thin film that resides on or just below the interior or exterior surface of the structural support 306.

In one embodiment, forming the induction coil 302 as a thin film conductor can be accomplished in a number of ways. For example, the induction coil 302 can be formed using either chemical or physical deposition techniques. Example of these techniques include, but are not limited to, chemical vapor deposition (CVD), plasma assisted CVD, thin film growth, sputtering, evaporation (thermal and e-beam), ion vapor deposition, and laser and/or electron beam assisted processing (e.g., laser ablation processing). As will be appreciated, the induction coil 302 can have a thickness sufficient to both receive RF energy and conduct the energy through the resonator device 300. For example, the induction coil 302 can have a thickness of about 10 microns or less.

As discussed herein, stents and other metallic implants can cause partial shielding of a RF field by the Faraday Effect. As a result, it has been difficult to obtain MRI visibility inside an implant. In an effort to obtain a better MRI visibility the implant can be positioned inside of the RF field of a local (implanted) resonating circuit, as discussed herein, that is tuned to the RF-frequency of the MRI system. The resonator-coil will cause the RF-field (as sent out by the MRI coil) to be magnified inside the coil. The result is to raise the energy level at the position of the implant without heating other parts of the body.

Embodiments of the resonator device can be used in association, or in conjunction, with a second medical device. For example, the resonator device can be provided over at least a part of the second medical device. In another example, the resonator device can be provided within at least a part of the second medical device. In an additional example, the resonator device can be integrated with (e.g., woven with and/or through) at least a part of the second medical device. The resonator device in conjunction with the second medical device can then operate in the presence of an electromagnetic field produced by an MRI system to reduce the artifacting (signal loss) in images obtained by an MRI system.

Figure 4:
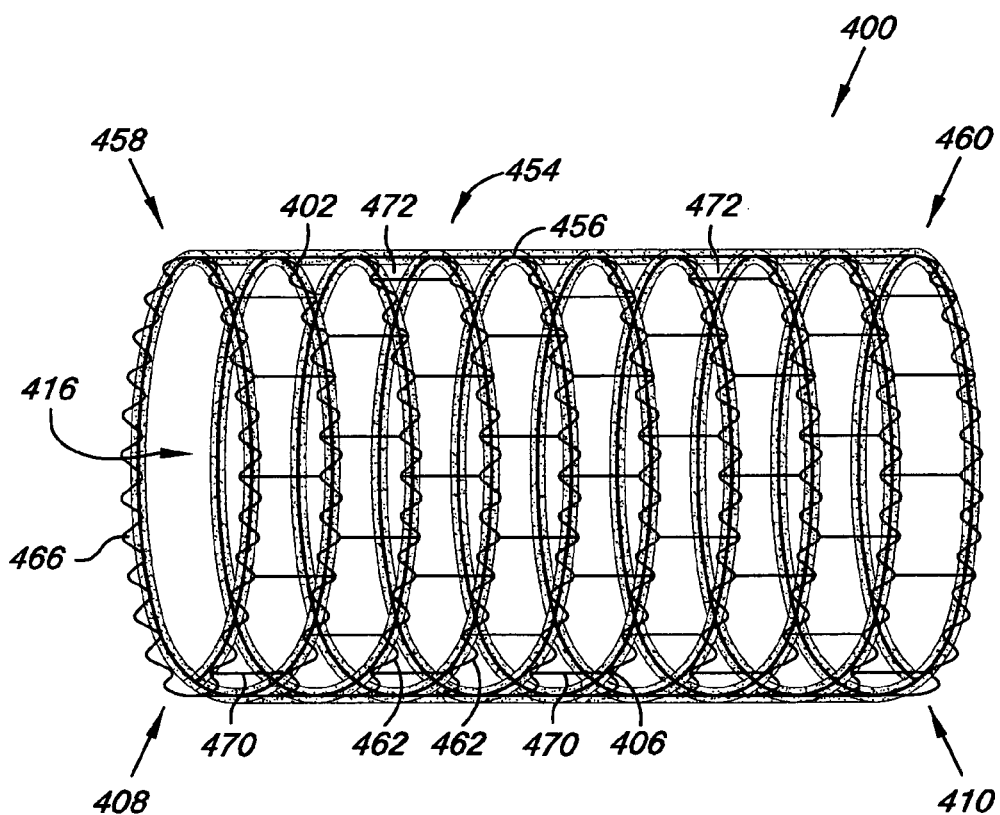
FIG. 4 illustrates an embodiment of a resonator device according to the present invention used in conjunction with a second medical device.

FIG. 4 illustrates one embodiment of the resonator device 400 associated with a stent 454. The stent 454 includes a tubular shaped body 456 having first and second ends 458 and 460 with elongate members 462 disposed between the first and second end 458 and 460. In one embodiment, the structural support 406 electrically insulates the resonator device 400 from the stent 454, where the resonator device 400 associates with the stent 454 through a mechanical interaction (e.g. a compressive friction fit).

As illustrated, the stent 454 can be positioned at least partially within, and be co-extensive with, the lumen 416 of the induction coil 402. For example, the stent 454 can be completely contained within the lumen 416 of the resonator device 400. As will be appreciated, being completely contained within the lumen 416 can include the situation where one or both of the ends of the stent 454 and the resonator device 400 meet essentially along a common plane. Alternatively, one or more of the ends 458 and 460 of the stent 454 can extend beyond one or more of the ends 408 and 410 of the resonator device 400.

The tubular shaped body 456 of the stent 454 includes a surface defining a lumen 466 having a first diameter, d, that permits intraluminal delivery of the tubular shaped body 456 into a body passageway, e.g., a lumen of the vasculature. The tubular shaped body 456 can be expanded to a second diameter, d', from force applied to the tubular shaped body 456, where the second diameter d' can be variable in size depending upon the amount of force applied to the tubular shaped body 456. In one embodiment, the stent 454 can either be a balloon expandable stent or a self-expanding stent.

The elongate member 462 can be formed of a material which has the requisite strength and elasticity characteristics to permit the tubular shaped body 456 to be expanded from the first diameter, d, to the second diameter d'. The material also allows the tubular shaped body 456 to retain its expanded configuration with the second diameter. Examples of such materials include, but are not limited to, tantalum, stainless steel, titanium, memory metal alloys (such as Nitinol), or any suitable plastic material having the requisite characteristics described herein.

The elongate member 462 can have a cylindrical cross-section, but as will be appreciated the elongate member 462 could have other cross-sectional configurations, such as triangular, square, rectangular, and/or hexagonal, among others. As illustrated, the elongate member 462 can be configured as a continuous helix of connected spirals or loops having a sinuous or zig-zag configuration. The elongate member 462 can also be fixedly secured to one another at predetermined intersection points and connectors 470 so as to help resist radial collapse of the stent 454 and to help maintain its enlarged diameter, d'. The predetermined intersection points and curved connectors 470 help to define openings 472 through the stent 454.

Figure 5:
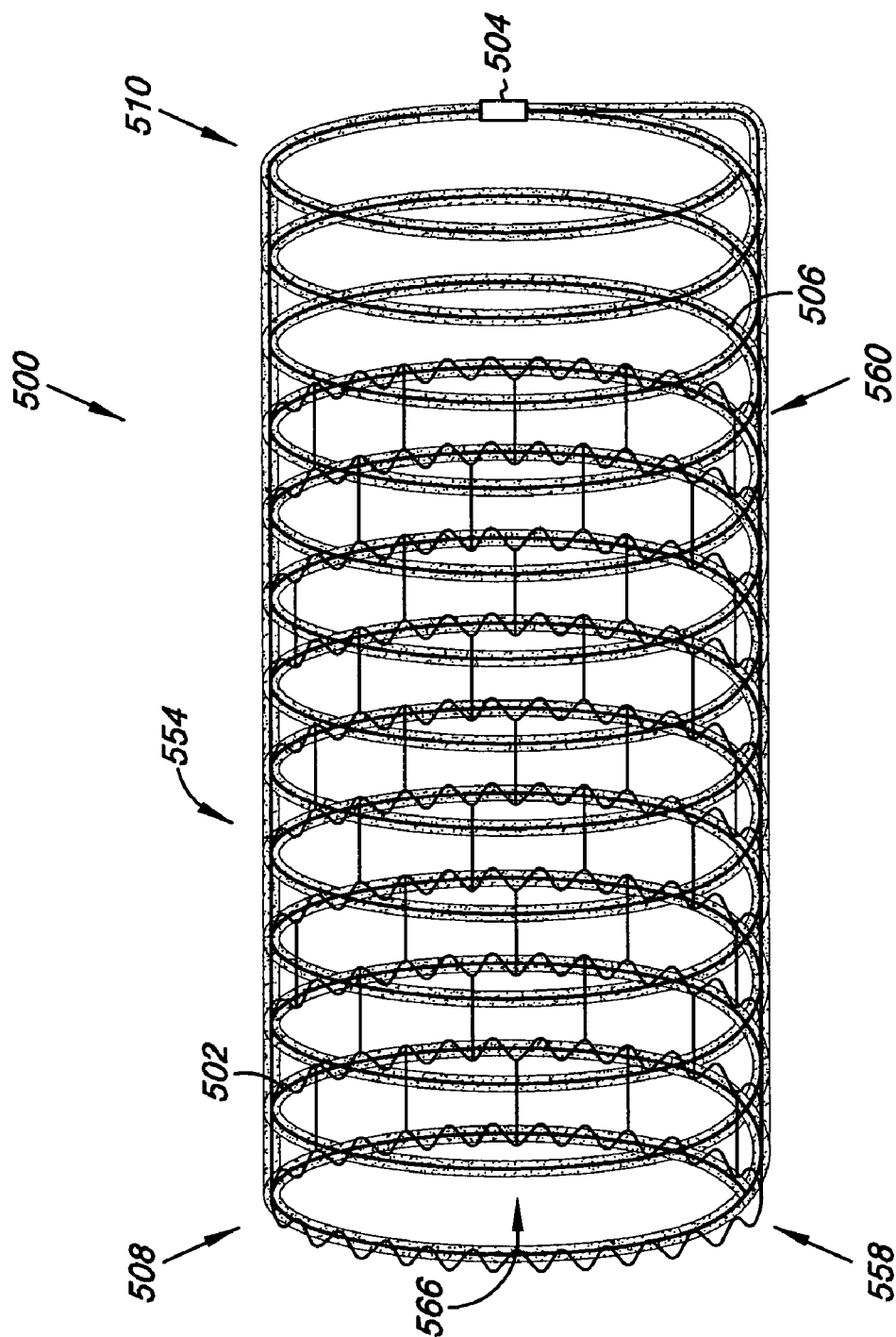
FIG. 5 illustrates an embodiment of a resonator device according to the present invention used in conjunction with a second medical device.

In an alternative embodiment, the stent can be positioned outside and be co-extensive with the lumen of the resonator device induction coil. For example, as illustrated in FIG. 5 there is shown the stent 554, as generally described herein. In one embodiment, the structural support 506 electrically insulates the resonator device 500 from the stent 554, where the resonator device 500 associates with the stent 554 through a mechanical interaction (e.g. a compressive friction fit). So, for example, the stent 554 could be first implanted within a patient, who subsequently receives the resonator device 500 positioned at least partially within the lumen 566 of the stent 554.

As will be appreciated, the induction coil 502 of the resonator device 500 can have a number of positions relative the ends 558 and 560 of the stent 554. For example, the first end 508 and the second end 510 of the induction coil 502 can extend beyond the ends 558 and 560 of the stent 554. Alternatively, one of the first end 508 or the second end 510 of the induction coil 502 can extend beyond the adjacent ends 558 and 560 of the stent 554.

Figure 6:
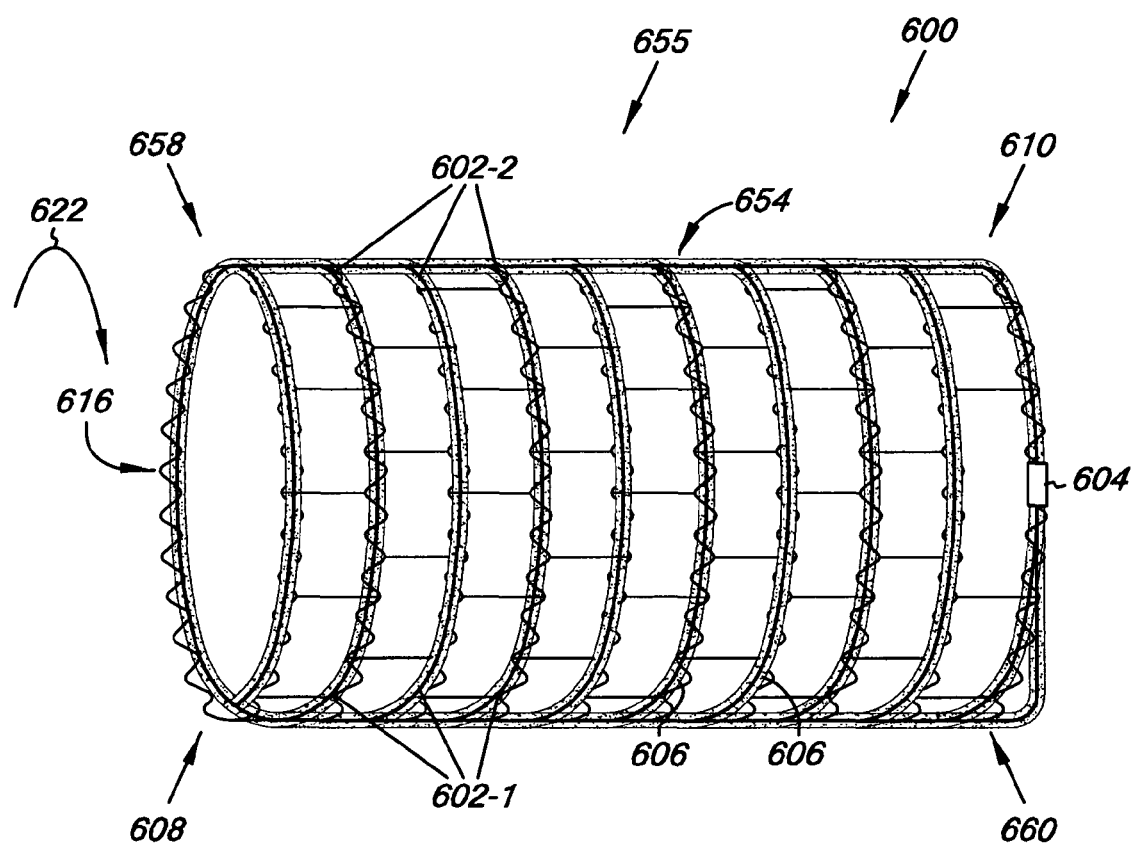
FIG. 6 illustrates an embodiment of a resonator device according to the present invention used in conjunction with a second medical device.

FIG. 6 illustrates an embodiment of a system 655 that includes a resonator device 600 having a first induction coil 602-1 and a second induction coil 602-2 positioned at least partially surrounding the stent 654. As illustrated, the two or more turns 622 of the first and second induction coils 602-1, 602-2 extend in the same direction. Other turn configurations for the induction coils are possible.

In addition, the first and second induction coils 602-1, 602-2 can either be used in separate resonator devices (e.g., 600-1 and 600-2), or can be integrated into one resonator device 600. For example, capacitor 604 can be coupled in series to the first induction coil 602-1 and the second induction coil 602-2 to form one resonator device 600. Alternatively, when separate resonator devices are used the second induction coil 602-2 can be coupled in series with a second capacitor to form one resonator system, while the first induction coil 602-1 is coupled in series to the first capacitor to for another resonator system.

As will be appreciated, the structural support 606 can be used to electrically insulate the one or more resonator devices 600 from the stent 654, and each other when two resonator devices are used. In addition, the structural support 606 can be in the form of a tube, as described herein, which encases one or both of the first and second induction coils. In one embodiment, the resonator device 600 associates with the stent 654 through a mechanical interaction (e.g. a compressive friction fit).

As illustrated, the stent 654 can be positioned at least partially between, and be co-extensive with, the coil lumen 616 of the induction coils 602-1 and 602-2. For example, the stent 654 can be completely contained within the lumen 616 of the resonator device 600. As will be appreciated, being completely contained within the lumen 616 can include the situation where one or both of the ends of the stent 654 and the resonator device 600 meet essentially along a common plane. Alternatively, one or more of the ends 658 and 660 of the stent 654 can extend beyond one or more of the ends 608 and 610 of the resonator device 600.

Implanting the resonator device 600 and the stent 654, as will be appreciated, will depend upon the configuration of the resonator device 600. For example, when discrete resonator devices 600 are used, a first of the resonator devices 600 can be implanted at a predetermined location with a patient. The stent 654 can next be positioned, as described herein, relative the first of the resonator devices 600. At this point, the stent 654 would be positioned at least partially within the lumen of the induction coil 602-1. A second of the resonator devices 600 can then be positioned at least partially within the lumen 666 of the stent 654 and at least partially within the coil lumen 616 of the first induction coil 602-1. In an alternative embodiment, the stent 654 and the resonator device 600 having integrated induction coils 602-1, 602-2 can be configured to be implanted into the patient as a unit.

As will be appreciated, the induction coils 602-1, 602-2 of the resonator device 600 can have a number of positions relative the ends 658 and 660 of the stent 654. For example, the first end 608 and the second end 610 of the induction coil 602-1, 602-2 can extend beyond the ends 658 and 660 of the stent 654. Alternatively, one of the first end 608 or the second end 610 of either induction coil 602-1, 602-2 can extend beyond the adjacent ends 658 and 660 of the stent 654.

Figure 7:
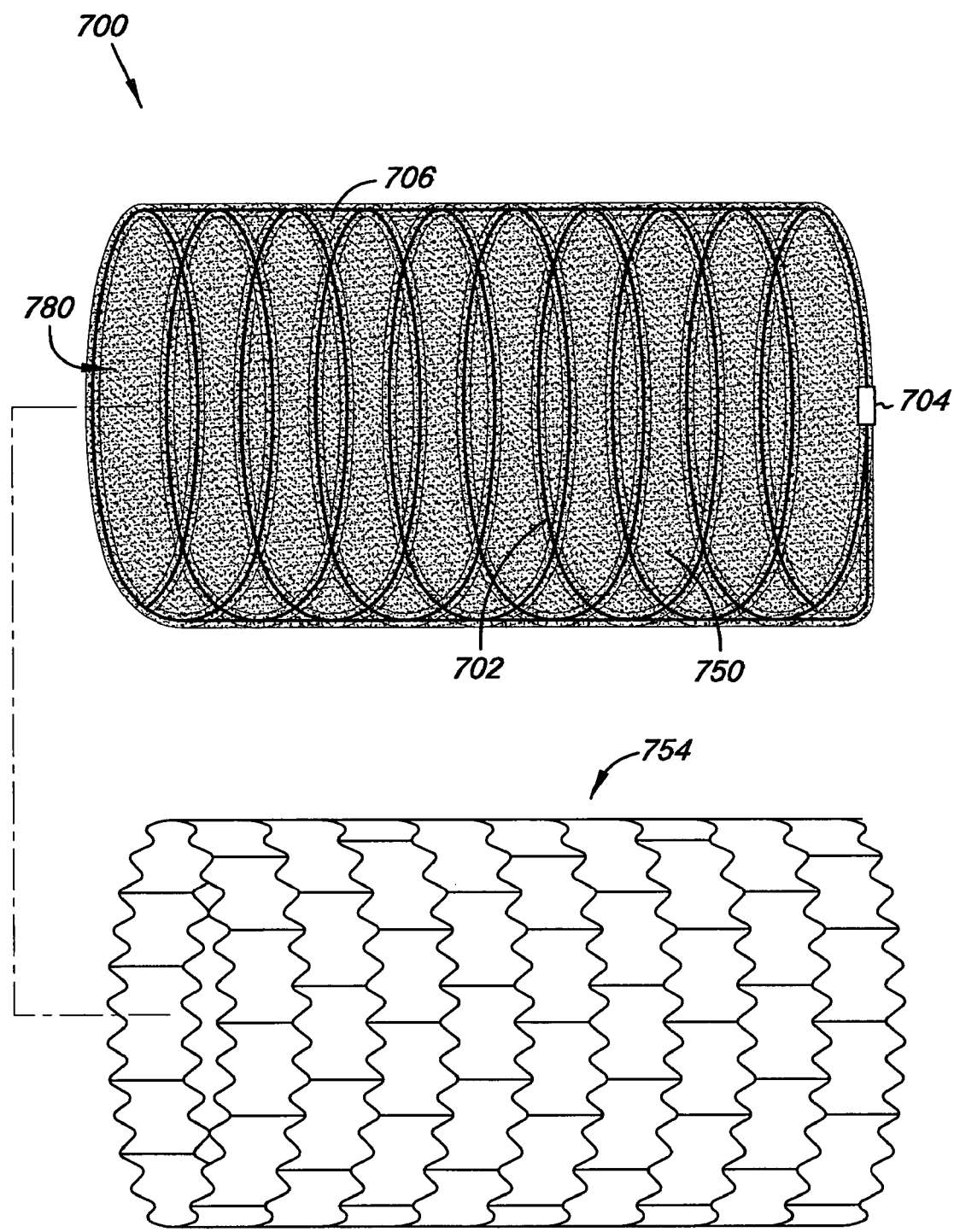
FIG. 7 illustrates an embodiment of a resonator device according to the present invention used in conjunction with a second medical device.

FIG. 7 illustrates an additional embodiment in which the resonator device 700 having structural support 706 is in the form of the tube 750, as discussed herein, is associated with the stent 754. As illustrated, the stent 754 can be positioned at least partially within the lumen 780 of the tube 750.

Figure 8:
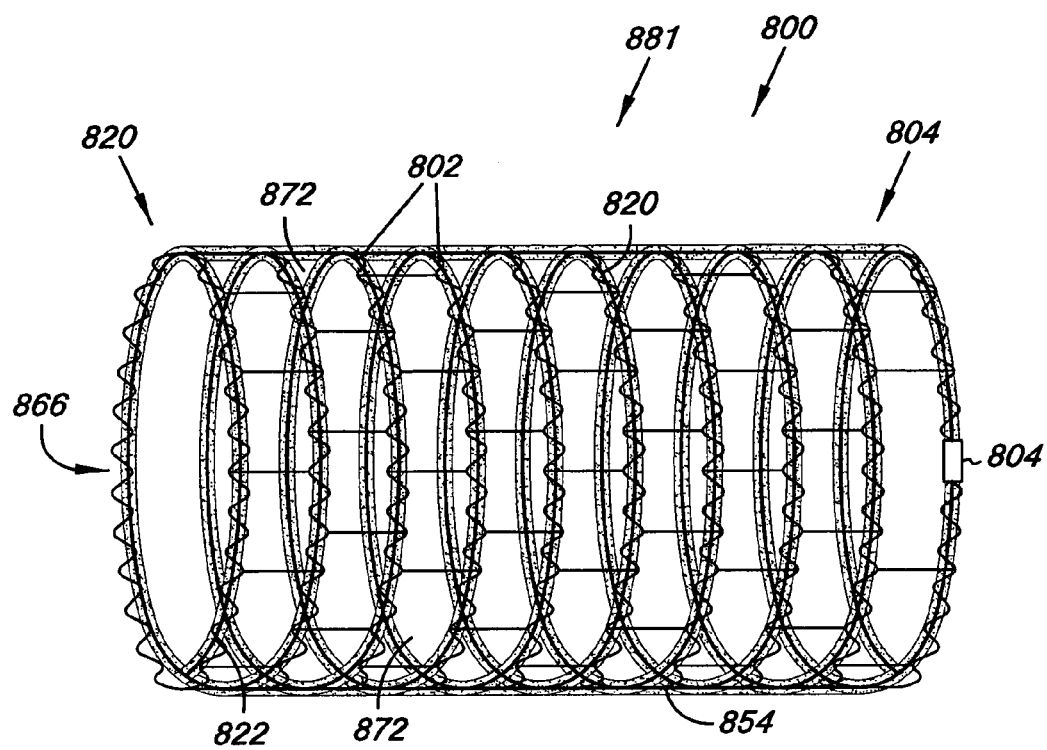
FIG. 8 illustrates an embodiment of a resonator device according to the present invention used in conjunction with a second medical device.

In an alternative embodiment, the stent and the resonator device can be produced so that the induction coil structure is woven at least partially through openings of the stent. FIG. 8 provides an illustration of an embodiment of a system 881 that includes the induction coil structure 802 of the resonance device 800 having a wound spiral of two or more turns 822 of the conductor that pass from the lumen 866 of the stent 854 through the openings 872 of the stent 854 to the outer surface of the stent 854.

For example, the induction coil structure 802 can pass from the lumen 866 of the stent 854 to the outer surface of the stent 854 on every complete turn of the induction coil structure 802. So, a first turn of the induction coil structure 802 can be positioned outside the lumen 866. As the second turn starts, the induction coil structure 802 passes through one of the openings 872 of the stent 854. The second turn can then be positioned within the lumen 866. As the third turn starts, the induction coil structure 802 then passes through another opening 872 of the stent 854. This pattern can then repeat itself along at least a portion of the stent 854.

In an alternative embodiment, other configurations for positioning the induction coil structure 802 at least partially within and at least partially outside the lumen 866 are also possible. For example, the induction coil structure 802 can pass two or more times from outside to within the lumen 866 during each turn of the induction coil structure 802. Alternatively, the induction coil structure 802 can be configured to have two or more loops 820 on the outside of the lumen 866, then to pass into the lumen 866 for two or more loops 820. This general pattern can then repeat along the length of the stent 854. In addition, each turn of the induction coil structure 802 need not have a linear configuration that extends continuously down the length of the stent 854. For example, the induction coil 802 can include a "zig-zag" configuration, as discussed herein.

The stent 854 and the induction coil structure 802 can be expanded from a first diameter that permits intraluminal delivery of the system 881 into a body passageway, e.g., a lumen of the vasculature, to a second diameter larger than the first diameter. In one embodiment, the diameter of the system 881 can be expanded from force applied to the stent 854 and the coil structure 802, where the second diameter can be variable in size depending upon the amount of force applied. In one embodiment, the force to expand the system 881 can be applied from balloon catheter system or from self-expanding members that form the stent 854 and/or the coil structure 802, as discussed herein.

Figure 9:
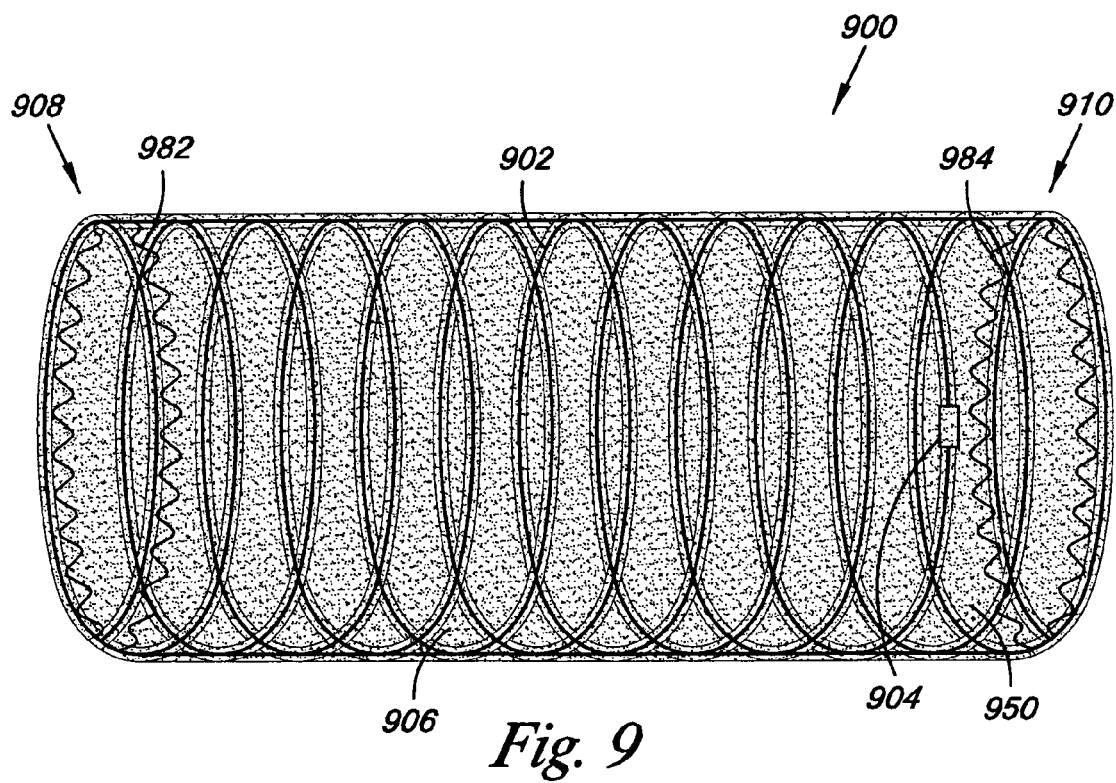
FIG. 9 illustrates an embodiment of a resonator device according to the present invention.

FIG. 9 provides an additional embodiment of the structural support 906 in relation to the induction coil 902 and capacitor 904. As illustrated, the structural support 906 is in the form of the tube 950 that supports the induction coil 902 and the capacitor 904, as discussed herein. In addition, the support structure 906 includes a first expandable support member 982 at the first end 908 and a second expandable support member 984 at the second end 910 of the support structure 906.

In one embodiment, the first and second expandable support members 982, 984 are electrically isolated from the induction coil 802. As illustrated, the first and second expandable support members 982, 984 can at least partially encircle the support structure 906. In one embodiment, the first and second expandable support members 982, 984 can include one or more rings that fully encircle the support structure 906. In an alternative embodiment, the first and second expandable support members 982, 984 are partial rings that either do not fully encircle the support structure 906 or have a helical configuration in which each respective support member 982, 984 does not form a closed and connected loop (i.e., the first and second expandable support members 982, 984 have a first and a second end that are uncoupled).

The first and second expandable support members 982, 984 are configured to change shape from a first diameter that permits intraluminal delivery of the resonator device 900 into a body passageway, e.g., a lumen of the vasculature, to a second diameter that is larger than the first diameter. In one embodiment, the first and second expandable support members 982, 984 can have a sinuous or a zig-zag pattern that encircles the support structure 906. As will be appreciated, this type of configuration allows the first and second expandable support members 982, 984 to be expanded from their first diameter to the second diameter.

The first and second expandable support members 982, 984 can be formed of a material which has the requisite strength and elasticity characteristics to permit the support members to be expanded from the first diameter to the second diameter. The material also allows the first and second expandable support members 982, 984 to retain their expanded configuration with the second diameter. Examples of such materials include, but are not limited to, tantalum, stainless steel, titanium, memory metal alloys (such as Nitinol), or any suitable plastic material having the requisite characteristics described herein.

In one embodiment, the first and second expandable support members 982, 984 help to secure the resonator device 900 at a predetermined position within a patient. For example, the resonator device 900 could be positioned upon a deflated balloon of a balloon catheter system. Upon positioning the resonator device 900 at a predetermined location within the patients, the resonator device 900 could be implanted by inflating the balloon to expand the first and second expandable support members 982, 984 so as to engage the resonator device 900 at the implant site. In an alternative embodiment, the first and second expandable support members 982, 984 can be self-expanding, where the catheter delivery system would constrain the first and second expandable support members 982, 984 in their first diameter until they were released at the implant site.

Figure 10:
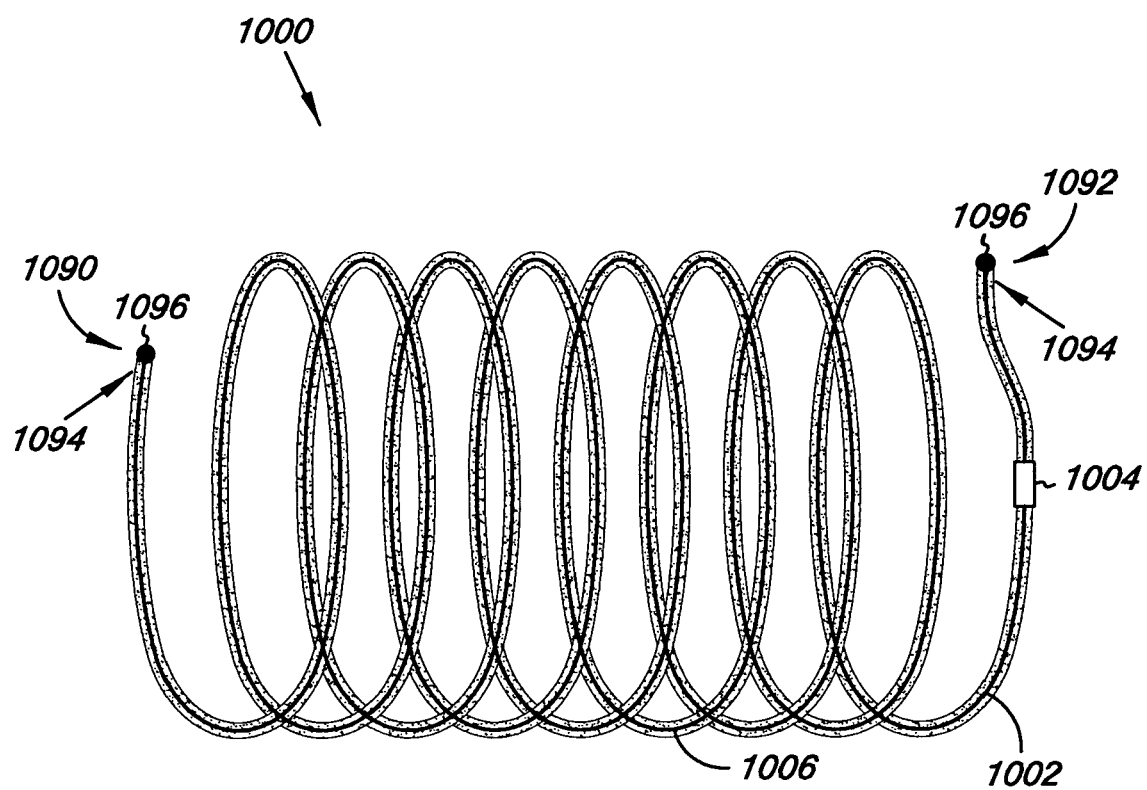
FIG. 10 illustrates an embodiment of a resonator device according to the present invention.

FIG. 10 provides an illustration of an additional embodiment of the resonator device 1000 according to the present invention. As illustrated, the resonator device 1000 includes the induction coil 1002, capacitor 1004 and structural support 1006, as discussed herein. In addition, the resonator device 1000 includes a first electrical contact 1090 and a second electrical contact 1092 electrically coupled to the induction coil 1002 and capacitor 1004. As illustrated, the first and second electrical contacts 1090, 1092 are located at or adjacent an end 1094 of the induction coil 1002. The first and second electrical contacts 1090, 1092 may also be positioned at other locations along the induction coil 102.

The first and second electrical contacts 1090, 1092 allow for electrically coupling the induction coil 1002 and capacitor 1004 with a stent, as discussed herein. In one embodiment, the first and second electrical contacts 1090, 1092 are configured as regions that can make electrical contact with a stent. For example, the first and second electrical contacts 1090, 1092 can include a conductive surface 1096 that extends beyond the outer diameter remaining portion of the coil lumen 1016. The resonator device 1000 can then be positioned within a stent. Upon expanding the induction coil 1002, the conductive surface 1096 of first and second electrical contacts 1090, 1092 can make contact with the lumen surface of the stent. Once in contact, the stent acts to complete the circuit of the resonator device 1000.

The first and second electrical contacts 1090, 1092 can include a number of different shapes and surface configurations. For example, the first and second electrical contacts 1090, 1092 can have a conical, hemispherical, semi-hemispherical, planar, or cylindrical shape. Other shapes are also possible. In addition, the conductive surface 1096 of the first and second electrical contacts 1090, 1092 can also include a texture that provides for a more positive electrical contact with the stent surface. For example, the conductive surface 1096 could have a predefined roughed texture that more easily engages the surface of the stent as compared to not having the predefined roughed texture. Examples include having sharp milled and/or knurled edges on the conductive surface 1096.

In an additional embodiment, the first and second electrical contacts 1090, 1092 can be initially covered with the structural support 1006. Upon expanding the induction coil 1002 within the lumen of the stent (e.g., through use of a balloon catheter or self-expanding structure), the conductive surface 1096 of first and second electrical contacts 1090, 1092 come into contact with the stent. As additional force is applied to expand the induction coil 1002, the conductive surface 1096 cuts through the structural support 1006 to allow electrical contact to be made with the stent, thereby completing the circuit of the resonator device 1000.

Figure 11:
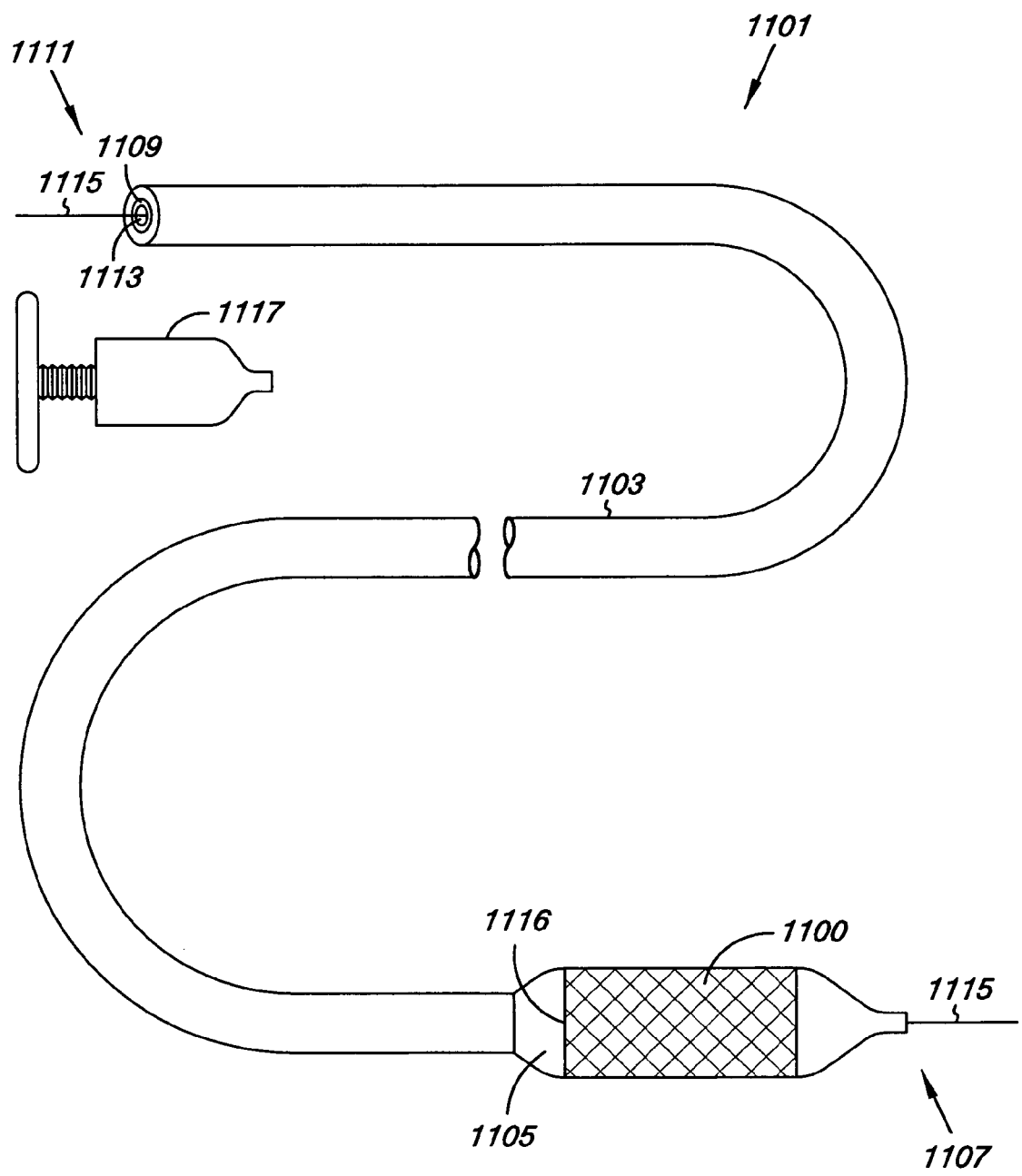
FIG. 11 illustrates an embodiment of a balloon catheter and a resonator device according to the present invention.

FIG. 11 illustrates a system having a catheter 1101 with an elongate body 1103, an inflatable balloon 1105 positioned adjacent a distal end 1107, and a lumen 1109 longitudinally extending in the elongate body 1103 of the catheter 1101 from the inflatable balloon 1105 to a proximal end 1111. In the present example, the inflatable balloon 1105 can be at least partially positioned within the lumen 1116 of the resonator device 1100.

The catheter 1101 can further include a guidewire lumen 1113 to receive a guidewire 1115. Guidewire 1115 and guidewire lumen 1113 assist in positioning the resonator device 1100, as discussed herein, at a predetermined location within the body. Once in position, the inflatable balloon 1105 can be inflated through the use of an inflation pump 1117 that can releasably couple to the lumen 1109. As the inflatable balloon 1105 inflates, the resonator device 1100 expands to the second diameter, as discussed herein, so as to position the resonator device 1100 in the patient.

While the present invention has been shown and described in detail above, it will be clear to the person skilled in the art that changes and modifications may be made without departing from the scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the resonator device can be coated with a non-thrombogenic biocompatible material, as are known or will be known, one or more pharmaceuticals and/or biological compounds or molecules.

Embodiments and illustrations described herein can further be modified and/or added to according to co-pending U.S. patent application Ser. No. 09/779,204, entitled "Vascular Stent with Composite Structure for Magnetic Reasonance Imaging Capabilities" [sic], which is incorporated herein by reference in its entirety.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A resonator device for implanting in a body, comprising:
   a first induction coil with a lumen having a deployed diameter;
   a second induction coil having a wound spiral of two or more turns positioned at least partially within the lumen of the first induction coil;
   a capacitor coupled in series to the induction coil that interacts with a radio frequency field to reduce signal loss in images obtained in a magnetic resonance imaging system;
   a non-conductive sheath coupled to the first induction coil and the capacitor; and
   a stent positioned at least partially between the first induction coil and the second induction coil.

2. The resonator device of claim 1, where the non-conductive sheath includes a predetermined configuration that supports and maintains the first induction coil in the deployed diameter.

3. The resonator device of claim 1, where the first induction coil includes a predetermined configuration that supports and maintains the first induction coil in the deployed diameter.

4. The resonator device of claim 1, where the stent includes a surface defining a lumen, and the first induction coil includes a wound spiral of two or more turns of a conductor, where the conductor passes the surface to position turns of the conductor within the lumen and outside the lumen of the stent.

5. The resonator device of claim 4, where the turns of the conductor alternate passing from within the lumen to outside the lumen.

6. The resonator device of claim 1, where the first induction coil is woven through openings in the stent.

7. The resonator device of claim 1, where the non-conductive sheath is a tube having a diameter that can expand to approximately equal the deployed diameter of the first induction coil.

8. The resonator device of claim 7, where the tube encases the first induction coil.

9. The resonator device of claim 7, where the tube includes a peripheral surface on which the first induction coil is positioned.

10. The resonator device of claim 7, where the first induction coil is a thin film conductor.

11. The resonator device of claim 7, where the stent is positioned at least partially within a lumen of the tube.

12. The resonator device of claim 7, where the tube includes a first end and a second end, the tube having a first expandable support member at the first end and a second expandable support member at the second end, where the first and second expandable support members are electrically isolated from the first induction coil.

13. The resonator device of claim 1, where the first induction coil includes a helical coil structure.

14. The resonator device of claim 13, where the helical coil structure includes a zig-zag configuration.

15. The resonator device of claim 1, where the non-conductive sheath includes one or more therapeutic agents.

16. The resonator device of claim 1, where the stent is positioned outside the lumen of the first induction coil.

17. The resonator device of claim 1, where the first induction coil includes a first electrical contact and a second electrical contact that electrically couple the first induction coil and the capacitor to the stent.

18. The resonator device of claim 1, where the first induction coil includes a first end and a second end opposite the first end, and where the deployed diameter of the lumen changes from the first end to the second end of the first induction coil.

19. A system, comprising:
    a stent having structural members defining a lumen, an outer surface opposite the lumen and openings between the structural members; and
    a resonator device having:
      a first induction coil that includes a wound spiral of a conductor that defines a coil lumen;
      a second induction coil having a wound spiral of two or more turns positioned at least partially within the lumen of the first induction coil;
      a capacitor coupled in series to the second induction coil that interacts with a radio frequency field to reduce signal loss in images obtained in a magnetic resonance imaging system; and
      a non-conductive sheath that electrically insulates the first induction coil from the stent, where the stent is positioned at least partially between the first induction coil and the second induction coil.

20. The system of claim 19, where the wound spiral of the first induction coil alternates passing from within the lumen to the outer surface of the stent.

21. The system of claim 19, where the first induction coil includes a zig-zag configuration.

22. The system of claim 19, where the first induction coil includes a non-conductive sheath that supports and maintains the wound spiral.

23. The system of claim 19, where the non-conductive sheath includes one or more therapeutic agents.

24. A system, comprising:
    a resonator device having:
      a first induction coil having a wound spiral of two or more turns of a conductor that define a coil lumen;
      a second induction coil having a wound spiral of two or more turns positioned at least partially within the coil lumen of the first induction coil; and
      a capacitor coupled in series with at least one of the first induction coil and the second induction coil; and
    a stent positioned at least partially between the first induction coil and the second induction coil.

25. The system of claim 24, where the capacitor is coupled in series to the first induction coil and the second induction coil.

26. The system of claim 24, including a second capacitor, where the first induction coil is coupled in series to the capacitor, and the second induction coil is coupled in series to the second capacitor.

27. The system of claim 26, where the first induction coil coupled in series to the capacitor is electrically insulated from the second induction coil coupled in series to the second capacitor.

28. The system of claim 24, where the resonator device includes a non-conductive sheath that supports the first and second induction coils.

29. The system of claim 28, where the non-conductive sheath is a tube having a diameter approximately equal the coil lumen of the first induction coil.

30. The system of claim 29, where the tube encases each of the first and second induction coils.

31. The system of claim 30, where the tube encases the stent.

32. The system of claim 28, where at least one of the first induction coil and the second induction coil is a thin film conductor.

* * * * *